[12] United States Patent
Andrews et al.

[10] Patent No.: US 7,615,057 B2
[45] Date of Patent: Nov. 10, 2009

(54) NOTCHED CUTTER FOR GUIDE CATHETER REMOVAL FROM LEAD

(75) Inventors: Christopher Charles Andrews, Lake Elsinore, CA (US); Neil M. Becker, Fallbrook, CA (US); Gayla Ann Smith, Canyon Lake, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 892 days.

(21) Appl. No.: 10/777,496

(22) Filed: Feb. 12, 2004

(65) Prior Publication Data

US 2005/0182435 A1 Aug. 18, 2005

(51) Int. Cl.
*A61B 19/00* (2006.01)
(52) U.S. Cl. ...................... 606/108; 606/129
(58) Field of Classification Search ........... 606/172, 606/108, 167, 129; 604/160; 607/119
See application file for complete search history.

(56) References Cited

U.S. PATENT DOCUMENTS

| 2,141,002 A | 12/1938 | Huff |
| 3,902,501 A | 9/1975 | Citron et al. |
| 4,394,828 A | 7/1983 | Garbis et al. |
| 4,451,256 A | 5/1984 | Weikl et al. |
| 4,631,059 A | 12/1986 | Wolvek et al. |
| 4,687,469 A | 8/1987 | Osypka |
| 4,997,424 A | 3/1991 | Little |
| 6,159,198 A | 12/2000 | Gardeski et al. |
| 6,497,681 B1 * | 12/2002 | Brenner ............... 604/164.05 |
| 2003/0181935 A1 * | 9/2003 | Gardeski et al. ........... 606/167 |

FOREIGN PATENT DOCUMENTS

| EP | 0 384 466 A1 | 8/1990 |
| EP | 0 587 267 A1 | 3/1994 |
| EP | 1 106 200 A2 | 6/2001 |

* cited by examiner

*Primary Examiner*—Anhtuan T Nguyen
*Assistant Examiner*—Amy T Lang
(74) *Attorney, Agent, or Firm*—Faegre & Benson LLP

(57) ABSTRACT

A device and method for removing a guide catheter from about a cardiac lead is disclosed. The device includes a blade for slitting the catheter so that the catheter may be removed from the lead. The blade includes upper and lower angled cutting surfaces which define a notch. The device includes a portion for receiving the lead and guiding the catheter to the blade.

9 Claims, 4 Drawing Sheets

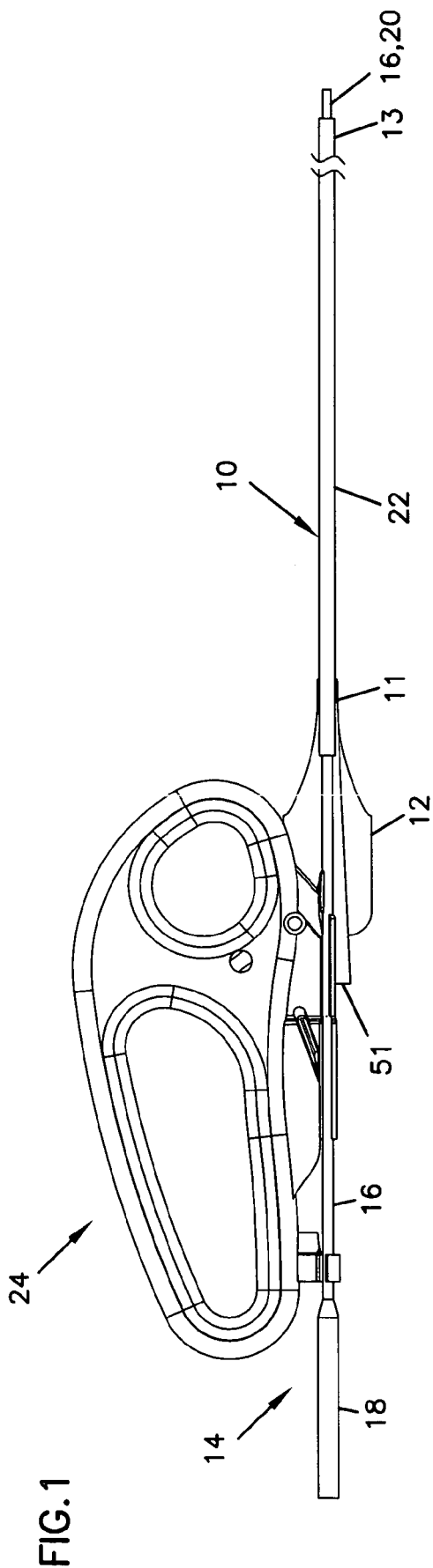

NOTCHED CUTTER FOR GUIDE CATHETER REMOVAL FROM LEAD

TECHNICAL FIELD

The present invention relates generally to devices for removing guide catheters from leads. More specifically, the present invention relates to notched cutters for slicing and removing guide catheters from implanted leads.

BACKGROUND OF THE INVENTION

Implanted medical devices, such as pacemakers or other cardiac rhythm management devices, often require that a lead be implanted within the body of a patient to connect the device with a specific portion of the patient's body, such as the heart. Minimally invasive techniques have been developed to permit these such leads to be implanted within the patient's body. One example of such a minimally invasive technique is to utilize a guide catheter, requiring only a relatively small incision at the insertion site.

Once the implanted lead has been positioned with the patient's body, the guide catheter needs to be removed from the lead. Often, the guide catheters include an outer sheath made of a reinforced material, such as a polymeric substrate with a steel mesh or reinforcing structure supporting the substrate. Such reinforced materials may be difficult to cut and may cause the cutter to bind, preventing the smooth removal of the catheter from about the lead and the withdrawal of the catheter from the patient's body.

Improvements to the tools and techniques used to remove a guide catheter from about a lead and from the patient's body are desirable.

SUMMARY

The present invention relates to a device for removing a guide catheter from about a linear object positioned within a lumen of the guide catheter. The device includes a body with a front edge, a rear edge, an upper edge and a lower edge. A web extends between the lower edge and a distal segment defining a central opening adapted to engage the linear object. The distal segment generally extends from the front edge toward the rear edge and includes an outer surface. The guide catheter extends about the outer surface as the linear object extends through the central opening of the distal segment. A blade is mounted between the lower edge and the outer surface of the distal segment and is supported by the web. The blade including a first cutting portion and a second cutting portion. The first cutting portion extends from the lower edge and is angled from the front edge toward the rear edge as the first cutting portion extends toward the distal segment. The second cutting portion extends from the distal segment toward the lower edge and is angled from the front edge toward the rear edge as the second cutting portion extends toward the lower edge. The first and second cutting portions of the blade form a notch between the lower edge and the distal segment. The blade is positioned to engage the guide catheter as the guide catheter passes about the outer surface of the distal segment.

The invention further relates to an assembly for removing a guide catheter from about a cardiac pacemaker lead. The assembly includes a guide catheter with a lumen within which the pacemaker lead is positioned. The pacemaker lead includes a distal end and terminal end, with a lead body extending between. The assembly also includes a cutter for removing the guide catheter from about the lead. The cutter includes a body with a front edge and a lower edge, and a lead management segment including a side opening arcuate member defining a central opening for receiving the lead positioned adjacent the lower edge. The lead management segment is connected to the body by a web. The lead management segment is adapted so that the guide catheter body passes over an outer surface when the lead is within the central opening. The cutter also includes a blade extending between the body and the lead management segment supported by the web. The blade includes a first portion extending from the body toward the lead management segment angling rearward with respect to the front edge, and a second portion extending from the lead management segment toward the body angling rearward with respect to the front edge. The first and second portions of the blade form a notch. The cutter is positioned about the lead adjacent the terminal end with the blade positioned to engage the guide catheter.

The present invention further relates to a method of removing a guide catheter from about an implantable cardiac lead. The implantable lead includes a terminal end and a distal end, and a lead body extending between. The guide catheter includes a lumen extending through a linear body with a distal end and a proximal end and a fitting mounted to the proximal end. The lead is positioned within the lumen of the guide catheter with the terminal end extending from the fitting of the guide catheter. Also provided is a cutter including a body with a front edge, a rear edge and a lower edge, a web extending from the lower edge and including a blade arranged toward the front edge. The web includes a lead management segment opposite the lower edge. The lead management segment includes an arcuate side-opening member defining a central opening for receiving the lead body. The blade includes a lower cutting edge adjacent the lead management segment extending rearwardly toward the lower edge and an upper cutting surface adjacent the lower edge extending rearwardly toward the lead management segment. The upper and lower cutting edges define a notch in the blade. The cutter is positioned about the lead body with the lead body positioned within the opening of the lead management segment and the front edge of the cutter toward the fitting of the guide catheter. The blade engages the fitting of the guide catheter. While holding the lead in position relative to the cutter, the guide catheter is drawn rearward along the lead so that the blade engages and slits the guide catheter. The slit guide catheter is removed from about the lead.

BRIEF DESCRIPTION OF THE DRAWINGS

The accompanying drawings, which are incorporated in and constitute a part of the description, illustrate several aspects of the invention and together with the detailed description, serve to explain the principles of the invention. A brief description of the drawings is as follows:

FIG. 1 is a perspective view of a guide catheter cutter according to the present invention mounted about an implantable cardiac lead in position to remove a guide catheter from about the lead, with a luer hub at the proximal end of the lead partially cut by the cutter.

FIG. 2 is a perspective view of the cutter of FIG. 1, removed from the cardiac lead.

DETAILED DESCRIPTION

Figure 3:
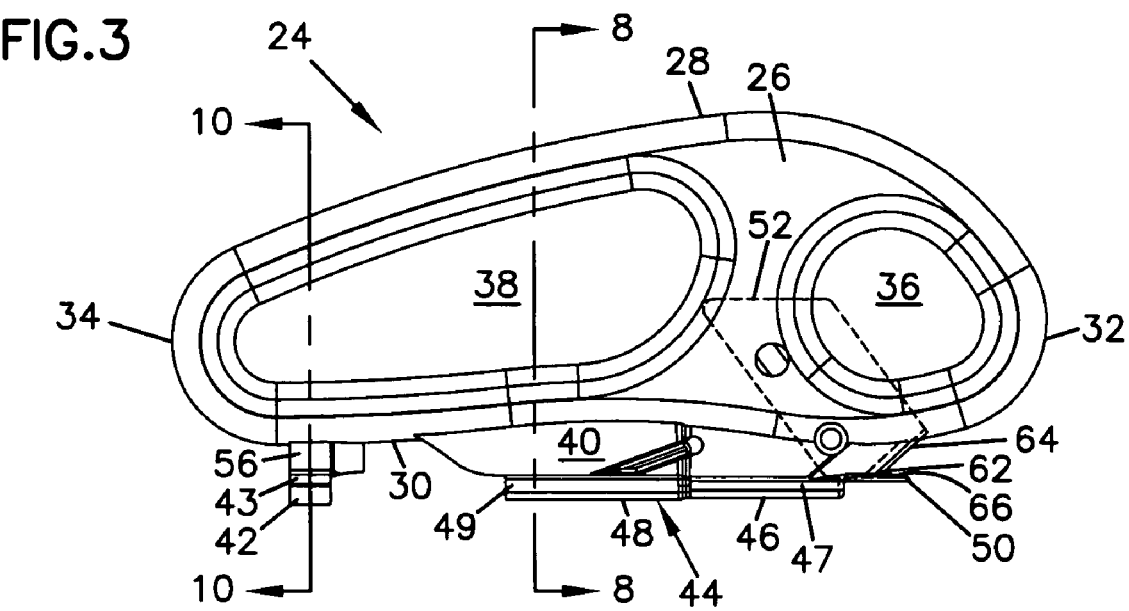
FIG. 3 is a first side view of the cutter of FIG. 2, with a blade for cutting the guide catheter within the cutter shown by dashed lines.

Reference will now be made in detail to exemplary aspects of the present invention which are illustrated in the accompanying drawings. Wherever possible, the same reference numbers will be used throughout the drawings to refer to the same or like parts.

When cardiac pacemakers or other implanted electro-stimulus devices are implanted in a patient's body, a lead may be used to connect the device to an area of the patient's body where the stimulus is desired. While such implantation procedures are necessarily invasive, techniques and devices have been developed to reduce the size and extent of invasion required. When implanting leads within or adjacent to a patient's heart for connection to a pacemaker, it is known to use a guide catheter to position the distal end of the lead in the desired location. Guide catheters may include a central axial lumen within which the lead is placed. The distal end of the guide catheter is then maneuvered so that the lead is properly placed within or adjacent the patient's heart. Such a guide catheter permits precise location of the distal end while requiring only a fairly small incision. Such catheter devices and techniques are well known.

Once the pacemaker lead has been positioned, the guide catheter must be removed from about the lead. Often these guide catheters include a luer hub or other similar fitting at a proximal end and a linear body extending from the fitting to the distal end of the catheter. A proximal end 11 of such a guide catheter 10 with a proximal fitting 12 (shown as a luer hub) is shown in FIG. 1. A cardiac lead 14 includes a linear lead body 16 inserted within a central axial lumen of a linear body 22 of catheter 10 and a terminal end 18 which is configured to be connected with a pacemaker (not shown) and extends from proximal end 11 of catheter 10. Lead body 16 defines a smaller diameter than terminal end 18. Lead body 16 includes a distal end 20 which is positioned adjacent distal end 13 of catheter 10.

Removal of catheter 10 from about lead 14 should be preferably accomplished without disturbing or displacing distal end 20 of lead 14. However, to keep catheter 10 to the smallest possible diameter to minimize the invasiveness of the placement procedure, and to reduce bleed back pressure during placement, the central axial lumen of linear body 22 of catheter 10 is sized to closely fit about lead body 16. Linear body 22 is not sized to be removed across terminal end 18. Thus it is advantageous to have a guide catheter cutter 24 to slit catheter 10 lengthwise and permit removal of guide catheter 10 from about lead 14.

Figure 4:
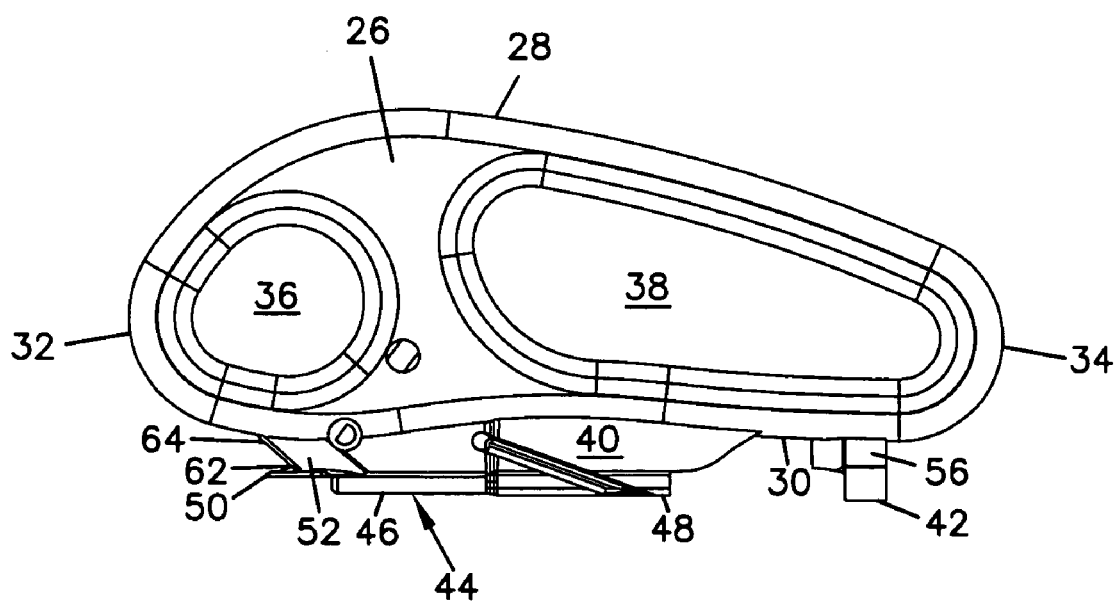
FIG. 4 is a second opposite side view of the cutter of FIG. 2.

Referring now to FIGS. 2 to 4, cutter 24 includes a handle 26 with an upper edge 28, a lower edge 30, a front edge 32 and a rear edge 34. In either side of handle 26 are a pair of gripping recesses 36 and 38. Extending from lower edge 30 adjacent front edge 32 is a web 40 which in conjunction with handle 26 supports a blade 52. Blade 52 is positioned within handle 26 and web 40 is a position as shown by the hidden lines in FIG. 3. Opposite handle 26 on web 40 is a distal lead management segment 44 with a forward portion 46 defining a smaller diameter and a rear portion 48 defining a larger diameter. Distal lead management segment 44 defines a central opening 58 (shown in FIGS. 5, 6 and 7) within a side opening 47 in forward portion 46 and a side opening 49 in rear portion 48. The side openings 47, 49 are configured to deform away from the lower edge of the lead body so as to enlarge the side opening allowing lead 14 to be snapped into central opening 58 from the side.

Extending from lower edge 30 adjacent rear edge 34 is a proximal lead management segment 42. As shown, proximal lead management segment 42 is connected to lower edge 30 by a web 56. Alternatively, proximal lead management segment 42 may be directly mounted to lower edge 30. Proximal lead management segment 42 defines a central opening 60 (shown in FIGS. 6, 7, and 10, below), axially arranged with central opening 58. A side opening 43 allows lead 14 to be snapped into opening 60 from the side.

A forward extension or nose 50 extends from the front of web 40 forward of blade 52. As shown in FIG. 1, luer hub 12 includes a proximal end 51, opposite proximal end 11 of catheter body 22, which is flared or larger in diameter than lead body 16. This flared end 51 permits a device such as a blood back flow valve or hemostasis valve to be removably fitted to luer hub 12. Flared end 51 also permit nose 50 to be inserted within luer hub 12 along lead body 16 so that blade 52 can engage and cut luer hub 12 and catheter body 22 from about lead 14. Web 40 also includes a pair of wings 54 on either side of web 40 proximate the transition from first portion 46 and second portion 48. These wings serve to force catheter 10 from about lead 14 once blade 50 has slit catheter 10 and catheter 10 has been moved proximally along lead 14. Catheter 10 is positioned about forward portion 46 until wings 54 urge catheter 10 from about lead 14 and distal lead management segment 44. As shown in FIG. 1, nose 50 is within the lumen of catheter 10 and blade 52 how just begun to slit luer hub 12. Flared end 51 of luer hub 12 has not yet reached wings 54.

Figure 5:
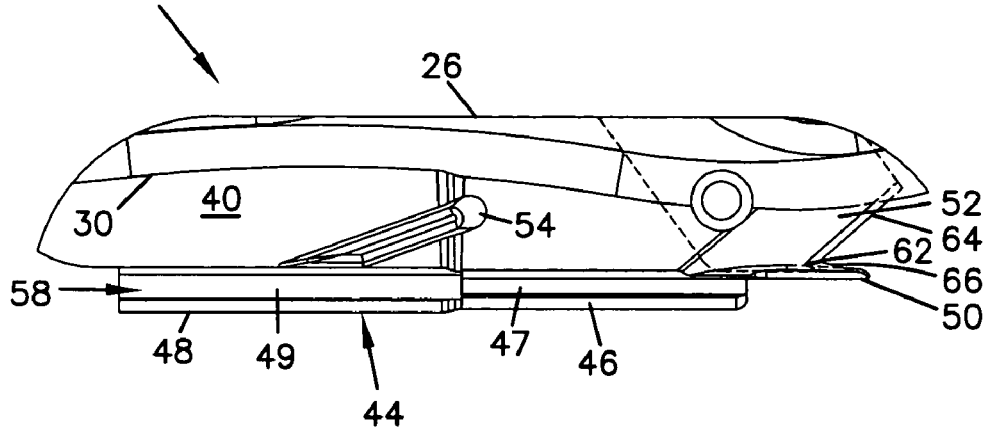
FIG. 5 is a first enlarged view of the cutter of FIG. 2, showing the cutting edge of the blade and a forward lead engaging structure.

Referring now also to FIG. 5, blade 52 includes an upper cutting edge 64 and a lower cutting 66, defining a notch 62 therebetween. Upper cutting edge 64 extends forwardly from notch 62 into lower edge 30 of handle 26. Lower cutting edge 66 extends forwardly from notch 62 into nose 50. Notch 62 thus defines the rearmost cutting portion of blade 52 and is positioned between nose 50 and lower edge 30 of handle 26. Notch 62 is preferably positioned adjacent nose 50. The positioning of notch 62 as the rearmost cutting portion of blade 52 provides improved resistance to binding of blade 52 during cutting or slitting of catheter 10 from about lead 14.

Guide catheters such as catheter 10, while flexible to aid insertion and placement of lead 14, may include a reinforcing material within linear body 22. This reinforcing material may be a steel or aramid mesh or braid embedded within body 22. This mesh, as well as the substrate material of linear body 22 must be cut by blade 52 to remove catheter 10 from lead 14. Cutters have rearwardly extending blades are known, and these blades may include forward edges to be inserted within the central lumen of catheter 10 to begin slitting catheter 10. However, catheter 10 and the reinforcing material within linear body 22 may resist slitting by the blade and may "climb" the rearwardly angled cutting edge, causing the blade to bind instead of smoothly and cleanly cutting linear body 22. Known cutter designs also may bind if the cutting of linear body 22 is stopped and started at an intermediate point between the distal and proximal ends.

Figure 11:
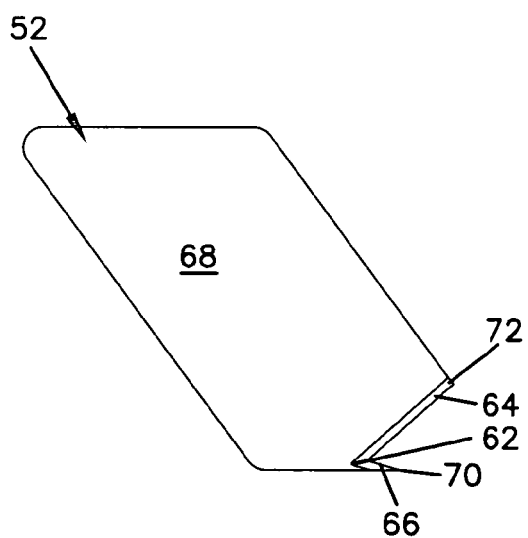
FIG. 11 is an enlarged view of the blade of the cutter of FIG. 2.

Lower cutting edge 66 of blade 52 adjacent nose 50 is angled forward from notch 62 to aid in insertion of blade 52 within the lumen of catheter 10. Above notch 62, upper cutting edge 64 is angled to prevent catheter 10 from climbing blade 52 away from nose 50 and causing cutter 24 to bind. An enlarged view of blade 52 is shown in FIG. 11. Blade 52 includes a body 68 which is enclosed within body 26 and web 40 of cutter 24. Lower cutting edge 66 includes a forward point 70 which is encased within nose 50. Upper cutting edge 64 includes a forward point 72 which is encased within body 26 adjacent lower edge 30 and front edge 32. Blade 52 may be preferably positioned within cutter 24 by having body 26, web nose 40 and nose 50 molded about blade 52, if cutter 24 is made of a moldable material. Other methods of construction and assembly may also be used for cutter 24. The configuration of notch 62 also improves the ability of cutter 24 to restart cutting of linear body 22 after stopping at an intermediate point between proximal end 11 and distal end 13.

Referring now to FIGS. 6 to 9, central opening 58 of distal lead management segment 44 is shown in greater detail. Side openings 47 and 49 permit lead body 16 to be snapped within central opening 58. Side openings 47 and 49 are slightly smaller in diameter than lead body 16. Distal lead management segment 44 is made of a resilient deformable material which permits entry of lead body 16 through openings 47 and 49 and then slidably and releasably holds lead body 16 within central opening 58. Forward portion 46 defines a smaller diameter than rear portion 48, and the diameter of forward portion 46 closely matches the diameter of lead 16. This permits lead body 16 to slide through forward portion 46 without excessive sideways movement. Nose 50 can then ride along lead body 16 to guide lower cutting edge 66 of blade 52 into the lumen of catheter 10 to slit catheter 10.

Beyond wings 54, distal lead management segment 44 defines a slightly larger diameter within rear portion 48. As cutter 24 is moved along lead body 16, catheter 10 is slit by blade 52 and urged from about lead 14 by wings 54. Rear portion 48 maintains control over the movement of lead 14 so that lead 14 can be separated from catheter 10. It is not necessary for rear portion to be as closely matched in size to lead body 16 and the enlarged diameter of rear portion 48 may reduce friction or other resistance to movement of cutter 24 along lead 14.

Figure 6:
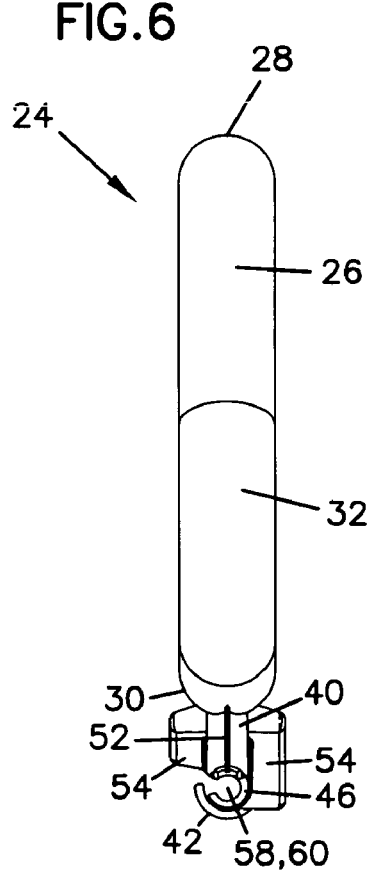
FIG. 6 is a front end view of the cutter of FIG. 2.
Figure 7:
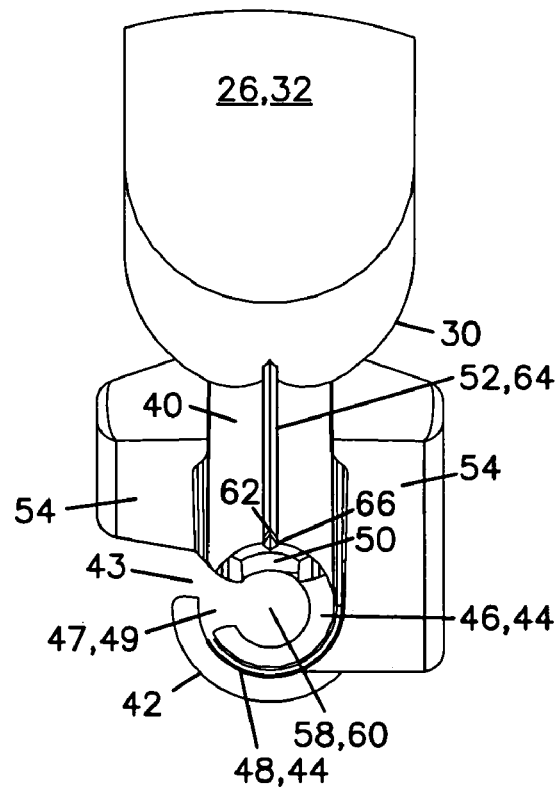
FIG. 7 is an enlarged front end view showing the cutting edge of the blade and the forward lead engaging structure.
Figure 8:
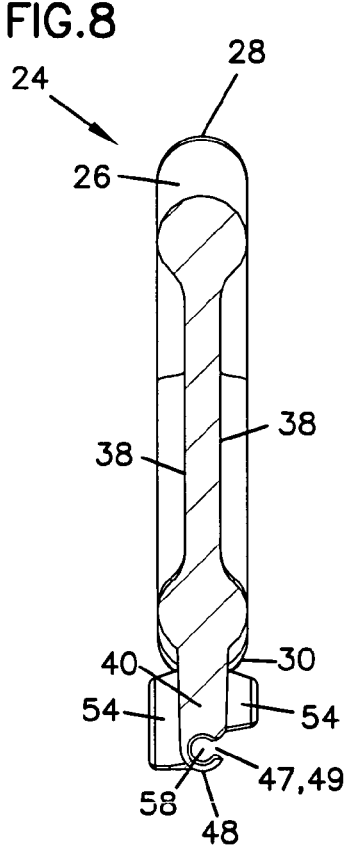
FIG. 8 is a first cross-sectional view of the cutter of FIG. 2, taken along line 8-8.
Figure 9:
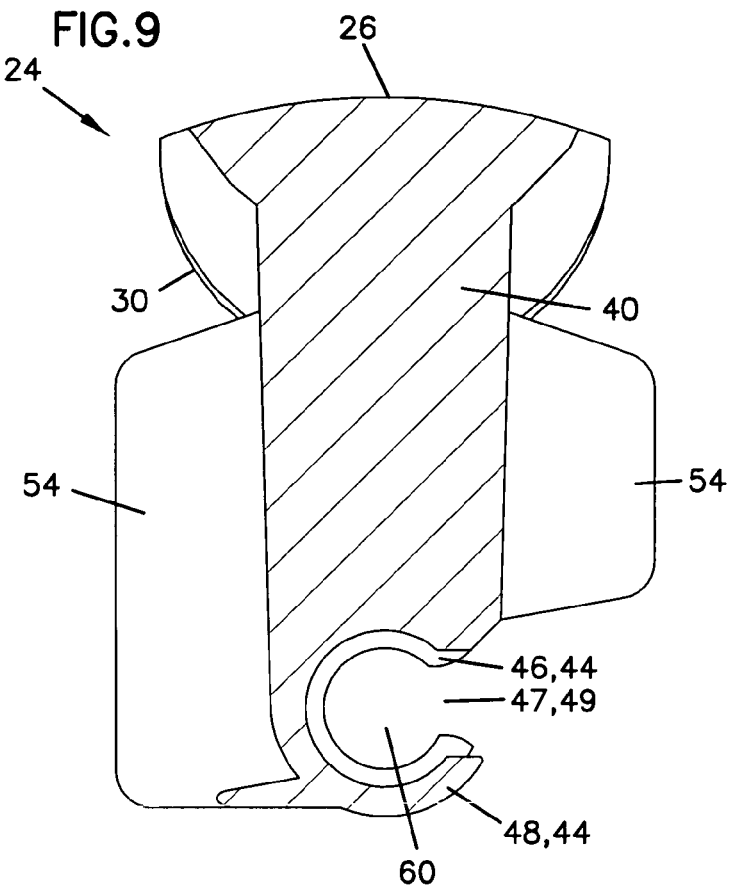
FIG. 9 is an enlarged view of the cross-sectional view of FIG. 9.
Figure 10:
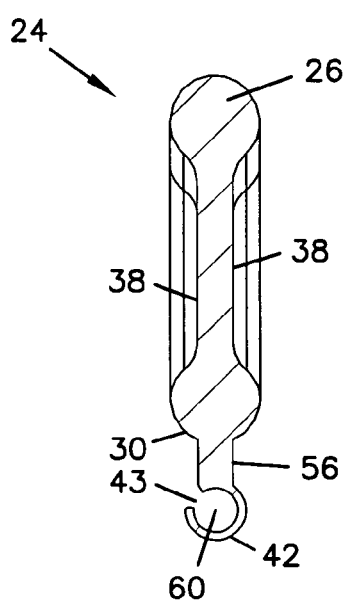
FIG. 10 is a second cross-sectional view of the cutter of FIG. 2, taken along line 10-10.

Referring now to FIGS. 6, 7 and 10, second arcuate lead engaging portion 42 is shown. Central opening 60 of proximal lead management segment 42 is axially aligned with central opening 58 of distal lead management segment 44. Central opening 60 is larger in diameter than either front portion 46 or rear portion 48 of distal lead management segment 44. Side opening 43 permits lead 14 to be snapped into opening 60, as proximal lead management segment 42 is constructed of a resilient deformable material, similar to distal lead management segment 44. Central opening 60 and side opening 43 may be made large enough to accommodate terminal end 18 of lead 14. Alternatively, central openings 58 and 60 and side openings 43 and 47 may be made the same size if accommodation of terminal end 18 is not required, or if a new terminal end is developed which is similar in diameter to the linear body 22.

In some implantation procedures, terminal end 18 of lead 14 may be positioned too close to luer hub 12 to permit lead body 16 to be snapped into both central opening 58 and central opening 60. For such situations, side opening 43 and central opening 60 may accommodate the larger diameter of terminal end 18. Cutter 24 can then be advanced along lead 14, slitting hub 12 and linear body 22 until lead body 16 is within opening 60, as shown in FIG. 1. At this position, cutter 24 can be held in position relative to lead 14 and catheter 10 moved rearward to completing the slitting and removal of catheter 10 from about lead 14. Alternatively, terminal end 18 can remain within central opening 60 as catheter 10 is pulled rearward to be slit and removed from about lead 14.

Once catheter 10 has been removed from about lead 14, lead 14 may be removed from central openings 58 and 60 of cutter 24 through side openings 43, 47, and 49.

The embodiments of the inventions disclosed herein have been discussed for the purpose of familiarizing the reader with novel aspects of the present invention. Although preferred embodiments have been shown and described, many changes, modifications, and substitutions may be made by one having skill in the art without unnecessarily departing from the spirit and scope of the present invention. Having described preferred aspects and embodiments of the present invention, modifications and equivalents of the disclosed concepts may readily occur to one skilled in the art. However, it is intended that such modifications and equivalents be included within the scope of the claims which are appended hereto.

What is claimed is:

1. A device for removing a guide catheter from about a linear object having a diameter positioned within a lumen of the guide catheter, the device comprising:

a body with a front edge, a rear edge, an upper edge and a lower edge;

a web extending from the lower edge of the body, the web including an upper portion and a lower portion having a web lower edge, the upper portion connected directly to the lower edge of the body;

a distal lead management segment having an outer surface and including a resiliently deformable side opening member extending in an arcuate manner from the lower portion of the web to a free edge so as to define a central opening having an inner diameter sized to engage the linear object, the web lower edge and the free edge spaced apart from one another such that they define a longitudinal side opening having a first dimension, the first dimension of the side opening being smaller than the diameter of the linear object and the inner diameter of the central opening, the side opening member configured to deform away from the lower edge of the lead body such that the free edge is moveable relative to the web lower edge so as to enlarge the side opening such that the linear object can be snapped into the central opening through the side opening, the side opening member further configured to retain the linear object within the central opening, the distal lead management segment extending directly from the lower portion of the web opposite the lower edge of the body such that the web extends directly from the lower edge of the body to the distal lead management segment, the distal lead management segment disposed between the front edge and the rear edge of the body and adapted so that the guide catheter may pass about the outer surface of the distal segment with the linear object positioned within the central opening of the distal lead management segment;

a blade mounted between the lower edge of the body and the outer surface of the distal segment and supported by the web;

the blade including a first cutting portion extending from the lower edge of the body which is angled from the front edge toward the rear edge as the first cutting portion extends toward the distal segment;

the blade including a second cutting portion extending from the distal segment toward the lower edge of the body which is angled from the front edge toward the rear edge as the second cutting portion extends toward the lower edge of the body;

the first and second cutting portions of the blade forming a notch between the lower edge and the distal segment; and the blade positioned to engage the guide catheter as the guide catheter passes about the outer surface of the distal segment.

2. The device of claim 1, wherein the notch is positioned proximate the distal segment.

3. The device of claim 1, wherein the device further includes a proximal segment with an arcuate side opening member defining a central opening, the proximal segment extending from the lower edge adjacent the rear edge and aligned with the distal segment, the central opening of the proximal segment sized to engage the linear object.

4. The device of claim 1, wherein the arcuate side opening member of the distal segment includes a forward smaller diameter portion and a rearward larger diameter portion.

5. The device of claim 4, wherein the web includes a pair of laterally extending opposing wings positioned rearward of the cutting portions of the blade, each wing angled rearward and downward to deflect the catheter from about the outer surface of the distal segment as the linear object passes through the distal segment.

6. The device of claim 5, wherein the distal segment defines a transition point between the smaller and the larger diameter portions and the wings are positioned adjacent the transition point.

7. The device of claim 4, wherein a nose extends forward from the smaller diameter portion of the distal segment and the nose is adapted to be inserted within and engage the lumen of the guide catheter.

8. An assembly comprising:
a guide catheter including a lumen;
a pacemaker lead having a diameter and including a distal end and terminal end with a lead body extending therebetween, the pacemaker lead receivable within the lumen of the guide catheter;
a cutter for removing the guide catheter from about the lead after placement of the lead, the cutter including:
a body with a front edge and a lower edge;
a web extending from the lower edge of the body, the web including an upper portion and a lower portion having a web lower edge, the upper portion connected directly to the lower edge of the body;
a lead management segment having an outer surface and including a resiliently, deformable side opening member extending in an arcuate manner from the lower portion of the web to a free edge so as to define a central opening having an inner diameter sized to engage the lead, the web lower edge and the free edge spaced apart from one another such that they define a longitudinal side opening having a first dimension smaller than the diameter of the lead, the side opening member configured to deform away from the lower edge of the body such that the free edge is moveable relative to the web lower edge to allow the lead to be snapped into the central opening, the side opening member further configured to retain the lead within the central opening, the lead management segment extending directly from the lower portion of the web opposite the lower edge of the body, such that the web extends directly from the lower edge of the body to the lead management segment, the lead management segment adapted so that the guide catheter body passes over the outer surface of the lead management segment when the lead is within the central opening;
a blade extending between the body and the lead management segment supported by the web, the blade including a first portion extending from the body toward the lead management segment angling rearward with respect to the front edge and a second portion extending from the lead management segment toward the body angling rearward with respect to the front edge, the first and second portions forming a notch;
the cutter positioned about the lead adjacent the terminal end with the blade positioned to engage the guide catheter.

9. The device of claim 1, wherein the web includes a pair of laterally extending opposing wings positioned rearward of the cutting portions of the blade, each wing angled rearward and downward to deflect the catheter from about the outer surface of the distal segment as the linear object passes through the distal segment.

* * * * *

UNITED STATES PATENT AND TRADEMARK OFFICE
CERTIFICATE OF CORRECTION

PATENT NO. : 7,615,057 B2  Page 1 of 1
APPLICATION NO. : 10/777496
DATED : November 10, 2009
INVENTOR(S) : Andrews et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1248 days.

Signed and Sealed this

Nineteenth Day of October, 2010

David J. Kappos
*Director of the United States Patent and Trademark Office*